Figure 1:
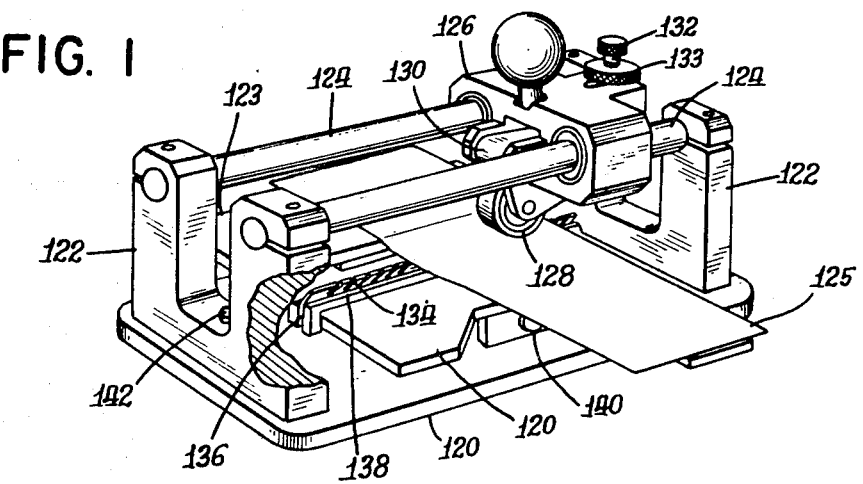

United States Patent [19]

Walter

[11] 4,231,273
[45] Nov. 4, 1980

[54] APPARATUS FOR PERFORATING A PAPER SAMPLE

[75] Inventor: Alfred Walter, Schlieren, Switzerland

[73] Assignee: Alfred Walter AG, Schliereh, Switzerland

[21] Appl. No.: 954,331

[22] Filed: Oct. 25, 1978

Related U.S. Application Data

[62] Division of Ser. No. 867,622, Jan. 6, 1978, Pat. No. 4,133,203.

[30] Foreign Application Priority Data

Jan. 10, 1977 [CH] Switzerland ............... 258/77

[51] Int. Cl.³ ............................................. B26D 3/08
[52] U.S. Cl. .................................................. 83/510
[58] Field of Search ............................. 83/510–512

[56] References Cited

U.S. PATENT DOCUMENTS

| 175,069 | 3/1876 | Giraudat | 83/512 |
| 593,878 | 11/1897 | Du Brul | 83/512 |
| 1,204,961 | 11/1916 | Baby et al. | 83/510 |
| 3,456,540 | 7/1969 | Manini | 83/512 X |
| 3,566,736 | 3/1971 | Johnson | 83/510 |
| 3,744,360 | 7/1973 | Currie | 83/510 X |

*Primary Examiner*—J. M. Meister
*Attorney, Agent, or Firm*—Fitch, Even, Tabin, Flannery & Welsh

[57] ABSTRACT

Apparatus for providing various different lines of perforations in a paper sample for use in a testing apparatus. The perforating apparatus includes a replaceable blade mounted on a base. A roller is mounted on the base for movement along the blade. Means are provided for adjusting the pressure applied by the roller to the paper sample disposed between the blade and roller.

2 Claims, 2 Drawing Figures

APPARATUS FOR PERFORATING A PAPER SAMPLE

This application is a division of my pending prior application Ser. No. 867,622 filed on Jan. 6, 1978, now U.S. Pat. No. 4,133,203.

The present invention relates to perforating apparatus and more particularly to an apparatus for providing various different lines of perforations in a paper sample for use in a testing apparatus.

Continuous forms, such as electronic digital processing (EDP) listing paper, normally contain lines of perforations which extend across the continuous form and serve as folding lines as well as separation lines of the individual forms. Other lines of perforations, which extend along the form, are found in snap-out and EDP listing paper. These with-the-web perforations serve as stub removals for EDP testing paper and internal vertical perforations on EDP listing paper or snap-out sets. Normally, the lines of perforation are made in the printing press after the actual printing of the form.

A common problem with such continuous forms is that the lines of perforations are too strong or too weak which can disturb the work of the forms user. If the perforations are too weak, the forms will burst in the printer of the computer. If, on the other hand, the perforations are too strong, the burster will not be able to separate the individual forms as desired and they may not refold in the computer stacker. This is also true of the vertical or with-the-web perforations which, when made too strong, will not come apart during the snap-apart operation of the "snap-out" set or if too loose, will prematurely fall apart. The burst strength of the line of perforations of a continuous or other form thereby should match the users methods of forms handling in order to give optimal results.

The desired burst strength of the lines of perforation, is affected by the machinery installed at the users plant, for example, printers and bursters, as well as by the paper strength and the folding units on the printing presses and collators. The burst strength of a line of perforation is determined by the ratio of cut and tie of a perforation in the line of perforations, by the sharpness of the perforating blade or wheel, the pressure of the perforator, and the paper quality. Two different production runs of the same type of paper, perforated under equal conditions, can give distinctly different results.

Therefore, it is important to enable production control at a forms printer to be in possession of precise and comparable figures in order to check continuously the burst strength in the production and to adjust it according to the forms users needs.

One such testing apparatus is disclosed in my prior pending application Ser. No. 867,622 filed on Jan. 6, 1978. It is desirable to provide paper samples with various lines of perforations so that the desired line of perforations may be selected by the operator of the testing apparatus.

An object of the present invention is to provide an apparatus for providing various lines of perforations in a paper sample for use in a testing apparatus.

Figure 2:
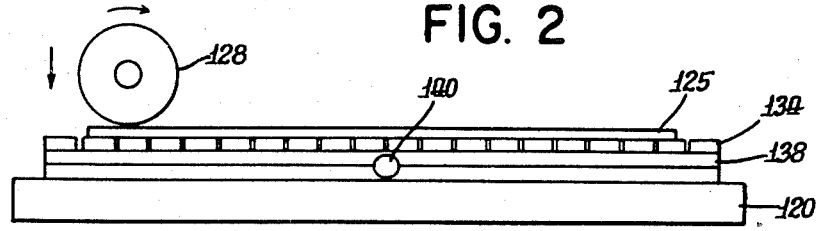

Other objects and advantages of the present invention will become apparent by reference to the following description and accompanying drawings wherein:

FIG. 1 is a perspective view of a perforating apparatus constructed in accordance with the present invention; and FIG. 2 is a schematic view of the perforating apparatus shown in FIG. 1.

More particularly, as shown in FIGS. 1 and 2, the perforating apparatus includes a base 120 having mounted thereon a pair of spaced U-shaped standards 122 and a pair of spaced horizontally extending plates 123 which serve as a bed for a paper sample 125. A pair of spaced, parallel, and horizontally extending rods 124 are fixedly attached to the legs of the standards 122. A carriage 126 is carried by the rods 124 for horizontal movement. The carriage carries a wheel 128 which is rotatably mounted to a lower end of an arm of a bell crank 130 that is pivotally mounted to the carriage. The other arm of the bell crank 130 bears against an adjustable pressure screw 132 which is locked in position by a lock screw 133. An elongated replaceable perforating blade 134 is disposed within a slot 136 in a holder 138 mounted to the base in the space between the bed plates 123. The blade 134 is maintained in the holder by a blade holder screw 140. To exchange blades 134, a screw 142 which limits leftward travel of the carriage 126 is removed and the carriage is moved onto the left standard 122. The blade holder screw 140 is loosened and then the blade may be lifted out of its holder.

The wheel 128 is arranged so that when the carriage 126 is moved manually, the wheel rides over the perforating blade 134 thereby perforating a form 125 disposed between the perforating blade 134 and the wheel 128. To adjust the pressure exerted by the wheel, the pressure screw 132 is adjusted.

By varying the perforating blade 134 and the pressure exerted by the roller 128 various lines of perforations may be obtained. By perforating across the grain or with the grain, the user can establish, prior to production, both vertical and horizontal perforations.

Various changes and modifications may be made in the above described apparatus without deviating from the spirit or scope of the present invention. Various features of the invention are set forth in the accompanying claims.

What is claimed is:

1. Apparatus for perforating a paper sample comprising a base including a pair of spaced, horizontally extending plates which serve as a bed for the paper sample, an elongated, replaceable perforating blade mounted in the space between said plates with the perforated edge extending above the surface of said plates, a pair of spaced, parallel and horizontally extending rods supported above and by said base, a carriage carried by said rods for horizontal movement, a bell crank pivotally mounted to said carriage with one arm extending below said carriage, a wheel rotatably mounted to said one arm of said bell crank so as to be moveable along said blade by movement of said carriage, and means for adjusting the spacing between said carriage and said other arm of said bell crank so as to adjust the pressure of said wheel against the blade, whereby when the carriage is moved the wheel rides over the perforating blade to perforate the paper sample disposed between the perforating blade and the wheel.

2. Apparatus in accordance with claim 1 wherein the adjusting means is a screw threadedly engaged with said carriage and bearing against said other arm of the bell crank.

* * * * *